(12) United States Patent
Rodriguez et al.

(10) Patent No.: US 8,871,725 B2
(45) Date of Patent: Oct. 28, 2014

(54) PHARMACEUTICAL COMBINATION FOR THE TREATMENT AND/OR CHEMOSENSIBILIZATION OF REFRACTORY TUMORS TO ANTICANCER DRUGS

(75) Inventors: Silvio Ernesto Perea Rodriguez, Ciudad De La Habana (CU); Yasser Perera Negrin, La Habana (CU); Arielis Rodriguez Ulloa, La Habana (CU); Jeovanis Gil Valdés, Ciudad De La Habana (CU); Yassel Ramos Gómez, Ciudad De La Habana (CU); Lila Rosa Castellanos Serra, Ciudad de La Habana (CU); Lázaro Hiram Betancourt Núñez, Ciudad De La Habana (CU); Aniel Sánchez Puente, Ciudad de La Habana (CU); Jorge Fernández de Cossio Dorta Duque, Ciudad De La Habana (CU); Boris Ernesto Acevedo Castro, Ciudad De La Habana (CU); Luis Javier González López, Ciudad De La Habana (CU); Vladimir Besada Pérez, Ciudad De La Habana (CU); Daniel Fernando Alonso, Buenos Aires (AR); Daniel Eduardo Gomez, Buenos Aires (AR)

(73) Assignee: Centro de Ingeniería Genética y Biotecnología, Ciudad de La Habana (CU)

( * ) Notice: Subject to any disclaimer, the term of this patent is extended or adjusted under 35 U.S.C. 154(b) by 1796 days.

(21) Appl. No.: 12/280,629

(22) PCT Filed: Feb. 28, 2007

(86) PCT No.: PCT/CU2007/000010
§ 371 (c)(1),
(2), (4) Date: Jan. 26, 2009

(87) PCT Pub. No.: WO2007/098719
PCT Pub. Date: Sep. 7, 2007

(65) Prior Publication Data
US 2009/0130228 A1 May 21, 2009

(30) Foreign Application Priority Data
Feb. 28, 2006 (CU) .................................. 2006-0049

(51) Int. Cl.
*A61K 38/08* (2006.01)
*A61K 39/00* (2006.01)
*C07K 7/06* (2006.01)
*A61P 35/00* (2006.01)
*A61K 45/06* (2006.01)
*A61K 33/24* (2006.01)
*A61K 31/555* (2006.01)

(52) U.S. Cl.
CPC ................. *A61K 45/06* (2013.01); *A61K 33/24* (2013.01); *A61K 31/555* (2013.01); *A61K 38/08* (2013.01)
USPC ....... 514/21.6; 514/19.3; 503/201; 424/181.1

(58) Field of Classification Search
None
See application file for complete search history.

(56) References Cited

U.S. PATENT DOCUMENTS

2004/0067953 A1* 4/2004 Stein et al. .................... 514/251

FOREIGN PATENT DOCUMENTS

| CU | EP-1491553 | * 12/2002 |
| EP | 1491553 | 12/2004 |
| WO | WO2005/056014 | 6/2005 |

OTHER PUBLICATIONS

Perea, S. Cancer Research, vol. 64, Oct. 1, 2004, pp. 7127-7129.*
Perea, 2004, Cancer Research, 64, 7127-7129.*
Perea, S. et al., Antitumor Effect of a Novel Proapoptotic Peptide that Impairs the Phosphorylation by the Protein Kinase 2 (Casein Kinase 2), Cancer Research, American Association for Cancer Research, Baltimore, MD, US, vol. 64, Oct. 1, 2004, pp. 7127-7129, XP002399575.
Piazza F. et al, "Multiple Myeloma Cells Survival and Proliferation Rely on High Levels and Activity of the Serine-Threonine Kinase CK2", Blood, vol. 104, No. 11, Nov. 16, 2004, p. 186A, XP009086788.

* cited by examiner

*Primary Examiner* — Satyanarayana R Gudibande
(74) *Attorney, Agent, or Firm* — Hoffmann & Baron, LLP

(57) ABSTRACT

This invention is related to a pharmaceutical combination that contains a Casein kinase 2 (CK2) peptide inhibitor (termed P15) along with the standard chemotherapeutic drugs used in cancer treatment and which are administered together, separated or sequentially. The chemotherapeutic drugs include cisplatin, taxol, alkaloids from Vinca, 5-fluorouracil, doxorubicin, cyclophosphamide, etoposide, mitomicin C, imatinib, iressa and velcade (vortezomib). The synergism between the P15 peptide and the anticancer drugs achieves an efficient concentration of each cytostatic drug in the combination which is from 10- to 100-fold lower than that for each cytostatic drug alone. The pharmaceutical combination described in this invention exhibits lower toxicity compared to that reported by the anticancer therapeutics and therefore, it represents a crucial advantage for its use in cancer therapy. Furthermore, the sequential administration of this pharmaceutical combination through the pretreatment with the P15 peptide leads to the chemo sensibilization of refractory tumors to the anticancer therapeutics.

11 Claims, 2 Drawing Sheets

A

B

C

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 1

Cys Trp Met Ser Pro Arg His Leu Gly Thr Cys
  1               5                  10
```

PHARMACEUTICAL COMBINATION FOR THE TREATMENT AND/OR CHEMOSENSIBILIZATION OF REFRACTORY TUMORS TO ANTICANCER DRUGS

This application is the U.S. National Phase of, and Applicants claim priority from, International Application Number PCT/CU2007/000010 filed 28 Feb. 2007 and Cuban Application bearing Serial No. CU 2006-0049 filed 28 Feb. 2006, which are incorporated herein by reference.

TECHNICAL FIELD

The present invention is related to the field of molecular and experimental oncology, in particular to the description of a pharmaceutical combination directed to the treatment and/or chemosensibilization of refractory tumors to conventional cytostatics.

PRIOR ART

In the last three decades, the use of chemical drugs as cytostatics for cancer therapy constitutes one of the choices as first-line treatment for some solid and hematopoietic tumors. The most commonly used chemical drugs for cancer therapy are: cisplatin, taxols, alcaloids from Vinca, doxorubicin, 5-fluorouracil, cyclophosphamide among others (Jackman A. L., Kaye S., Workman P. (2004) The combination of cytotoxic and molecularly targeted therapies-can it be done? *Drug Discovery Today* 1:445-454). However, results from clinical trials exhibit a low therapeutic index for this kind of drug in cancer therapy as evidenced by the marginal therapeutic benefit along with the high toxicity profile observed in the patients (Schrader C., et al. M. (2005) Symptoms and signs of an acute myocardial ischemia caused by chemotherapy with paclitaxel (taxol) in a patient with metastatic ovarian carcinoma. *Eur J Med Res* 10:498-501). For example, many authors agree that cisplatin constitutes the first-line treatment for lung cancer, however a modest efficacy is commonly observed with little improvement on the clinical symptoms and 6-weeks increase of survival (Grillo R., Oxman A., Julian J. (1993) Chemotherapy for advanced non-small cell lung cancer. *J Clin Oncol* 11:1866-1871; Bouquet P. J., Chauvin F., et al (1993) Polychemotherapy in advanced non-small cell lung cancer: a meta-analysis. *Lancet* 342:19-21). Therefore, the current strategies to achieve an optimal therapeutic benefit are focused to pharmaceutical combinations based on conventional cytostatic drugs along with molecular targeted therapies. Some of the current anticancer drugs are classified as cancer targeted therapy, for instance, Gleevec (Imatinib) which targets the Abl kinase that in turns play an essential role on the development of Chronic Myeloid Leukemia (Giles J. F., Cortes J. E., Kantarjian H. M. (2005) Targeting the Kinase Activity of the BCR-ABL Fusion Protein in Patients with Chronic Myeloid Leukemia. *Current Mol Med* 5:615-623), also Iressa that targets tyrosine kinase associated to the Epidermal Growth Factor (EGF) receptor (Onn A., Herbst R. S. (2005) Molecular targeted therapy for lung cancer. *Lancet* 366:1507-1508) and Velcade (Bortezomib) which blocks the protein degradation by targeting the proteasome machinery (Spano J. P., et al. (2005) Proteasome inhibition: a new approach for the treatment of malignancies. *Bull Cancer* 92:E61-66), among others. Considering that the non-specific mechanisms of the conventional chemotherapeutics converge on the abrogation of cellular mitosis, the use of the new cancer targeted therapeutics provides great perspectives to achieve pharmaceutical combinations which produce synergism of the antitumor effect.

On the other hand, drug resistance phenomenon is recognized as the primary cause of the failure on cancer therapy when chemotherapeutic agents are employed. In spite of that sub-optimal drug concentration on the tumor milieu could influence the drug resistance, other factors like cellular origin plays an essential role on the chemo resistance for many tumors. Drug resistance is a multifactorial phenomenon depending on multiple independent mechanisms which involve intracellular detoxification, changes on the cellular response, tolerance to stress and defects on the apoptosis signaling pathways (Luqmani A. (2005) Mechanisms of drug resistance in cancer chemotherapy. *Med Princ. Pract* 14:35-48). The Glycoprotein-P and the Gluthathion S-transferase are the major proteins that mediate the intracellular detoxification process linked to the drug resistance phenomenon in cancer (Saeki T., Tsuruo T., Sato W., Nishikawsa K. (2005) Drug resistance in chemotherapy for breast cancer. *Cancer Chemother Pharmacol* 56:84-89) (Hara T., et al. (2004) Gluthathione S-transferase P1 has protective effects on cell viability against camptothecin. *Cancer Letters* 203:199-207). Other proteins like beta-tubulins have been reported to be involved on the drug resistance phenomenon and whose levels directly correlate with the tumor resistance to Paclitaxel (Orr G. A., et al. (2003) Mechanisms of Taxol resistance related to microtubules. *Oncogene* 22:7280-7295). Otherwise, the cisplatin resistance has been reported to be influenced by the over expression of different proteins like T-plastin (Hisano T., et al. (1996) Increased expression of T-plastin gene in cisplatin-resistant human cancer cells: identification by mRNA differential display. *FEBS Letters* 397:101-107), the Heat Shock Protein (HSP70) and (HSP90) (Jaattela M. (1999) Escaping cell death: survival proteins in cancer. *Exp Cell Res* 248:30-43) and the transcription factor YB1 (Fujita T., et al. (2005) Increased nuclear localization of transcription factor Y-box binding protein accompanied by up-regulation of P-glycoprotein in breast cancer pretreated with paclitaxel. *Clin Cancer Res* 11:8837-8844). Additionally, exacerbation of Glycolisis and Piruvate pathways has been reported to play an essential role on the chemo resistance phenomenon observed in tumor cells (Boros L. G., et al. (2004) Use of metabolic pathway flux information in targeted cancer drug design. *Drug Disc. Today* 1:435-443).

Reports from different groups have indicated the existence of a set of proteins which either inhibit apoptosis or increase cell survival on tumor cells thus contributing to the chemoresistance phenomenon of tumors. One of the examples is the Nucleophosmin protein which plays a central role on cell cycle promoting, inhibition of apoptosis and it has been regarded as a poor prognosis marker in cancer (Ye K. (2005) Nucleophosmin/B23, a multifunctional protein that can regulate apoptosis. *Cancer Biol Ther* 4:918-923). Likewise, the CK2 enzyme plays an important role on cell survival and in the resistance of tumor cells toward apoptosis (Tawfic S., Yu S., Wang H., Faust R., Davis A., Ahmed K. (2001) Protein kinase CK2 signal in neoplasia. *Histol. Histopathol.* 16:573-582). Previous findings have revealed the elevation of CK2 activity from 3- to 7-fold in epithelial solid tumors respect to the normal tissues (Tawfic S., Yu S., et al. (2001) Protein kinase CK2 signal in neoplasia. *Histol Histopatol.* 16:573-582; Faust R. A., Gapany M., et al (1996) Elevated protein kinase CK2 activity in chromatin of head and neck tumors: association with malignant transformation. *Cancer Letters* 101:31-35). Furthermore, the CK2 activity is an important cellular event for the malignant transformation and it constitutes a tumor progression marker (Seldin D. C., Leder P. (1995) Casein Kinase IIα transgene-induced murine lymphoma: relation to theileroiosis in cattle. *Science* 267:894-897). The fact that the CK2 phosphorylation represents a strong signal to protect tumor cells from apoptosis, it leads to the consideration of this enzyme as an antiapoptotic mediator on cellular physiology (Ahmed K., Gerber D. A., Cochet C. (2002) Joining the cell survival squad: an emerging role for protein kinase CK2. *Trends Cell Biol*, 12:226-229; Torres J., Rodríguez J., et al (2003) Phosphorylation-regulated cleavage of the tumor suppressor PTEN by caspase-3: implications for the control of protein stability and PTEN-protein interactions. *J Biol Chem*, 278:30652-60).

Altogether, the CK2 phosphorylation is a biochemical event that represents a potential target for cancer therapy and specific inhibitors of this event could lead to drug candidates with perspectives cancer management.

Different groups have developed different strategies to inhibit the CK2 phosphorylation using two independent approaches. a) Direct inhibition of the CK2 alpha catalytic subunit, b) Direct targeting of the acidic domain on the CK2 substrates (patent WO 03/054002 and Perea S. E., et al. (2004) Antitumor effect of a novel proapoptotic peptide impairing the phosphorylation by the protein kinase CK2. *Cancer Res*. 64:7127-7129). Using both approaches, authors have demonstrated the proof-of-principle that the CK2 inhibition lead to apoptosis on tumor cells. These findings reinforce the experimental validation of CK2 as a suitable target to develop anticancer drugs.

The comparative proteomic studies along with the development of molecular biology have permit in part, the understanding of the molecular mechanisms involved both in cell malignant transformation and tumor chemoresistance. Therefore, cancer therapy regimens should focus their attention in achieving effective drug combinations which greatly reduce toxicity and also reduce the possibility of chemoresistance arising. Thus, one of the major goals today in cancer therapy is to increase the therapeutic index of the current cytostatic drugs by reducing the effective dose and the intrinsic toxicity displayed by this kind of medicines. Other current strategy is to bypass the tumor chemoresistance toward the conventional cytostatic drugs.

DETAILED DESCRIPTION OF THE INVENTION

This invention solves the problem above mentioned as it provides a pharmaceutical combination that contains two ingredients: a CK2 phosphorylation inhibitor (P15 peptide) and a cytostatic drug pharmaceutically acceptable.

In this invention, "cytostatic drug pharmaceutically acceptable" referrers to all the cytostatic chemical compounds used for cancer chemotherapy both for solid tumors and those from hematopoietic origin. The preferred cytostatics are cisplatin and carboplatin, paclitaxel and docetaxel, vincristine and vinblastine, 5-fluouracil, doxorubicin, cyclophosphamide, etoposide, mytomicin C, imatinib, iressa, and velcade (bortezomib) mixed with appropriated vehicles.

In this invention, the concept of "inhibition of CK2 phosphorylation" also includes any chemical or peptidic compound that blocks either the substrate or the enzyme itself. Depending on the situation, the active ingredients of this pharmaceutical combination can be administered simultaneously, separated o sequentially. The administration of this pharmaceutical combination can be performed by systemic, topic or oral routes. This invention also referrers to the treatment and/or the bypassing of the chemoresistance in refractory tumors occurring in human beings using the pharmaceutical combination mentioned above.

Likewise, this invention referrers to the use of the ingredients of this pharmaceutical combination to prepare a medicine to treat chemorefractory tumors and to increase the antitumor effect of the cytostatic drugs cited in this invention.

The example 1 (Table 1) shows that the pharmaceutical combinations described in this invention produce a synergistic antineoplastic effect in vitro. Thus, the simultaneous combination of sub-optimal doses from the P15 peptide along with cisplatin, paclitaxel, doxorubicin, vincristin, etoposide, mitomicin C, 5-fluouracil, imatinib, or iressa, achieves a 10- or 100-fold reduction of the effective dose for each cytostatic drug mentioned in this invention. Effective dose is that achieves a 50% of the antineoplastic effect which is also termed Inhibitory Concentration 50% (IC50) in proliferation assays in vitro. In this invention, "sub-optimal doses" referrers to those lower than the IC50.

The example 2 illustrates the potentiation of the antitumor effect in vivo by using this pharmaceutical combination containing the P15 peptide along with cisplatin (FIG. 1A), cyclophosphamide (FIG. 1B) and mytomicin C (FIG. 1C). The pharmaceutical combination leads to the complete tumor regression in a relevant animal model like that consisting in a human tumor xenografted in nude mice. However, the use of the ingredients of this pharmaceutical combination like monotherapy did produce only a marginal delay on tumor growth compared to the effect observed in placebo group.

The sequential administration of the ingredients from this pharmaceutical combination demonstrates that P15 treatment bypasses the tumor chemoresistance both in vitro and in vivo. In this invention, it is understood that "bypassing of tumor chemoresistance or chemosensibilization" referrers to the event of reducing the drug dose needed to produce the 50% of the antitumor effect after pretreatment with the P15 peptide. The example 3 illustrates the effect of P15 peptide pretreatment in the chemosensibilization of tumor cells and it produces from 10- to 100-fold reduction of the effective drug dose. Similarly, data showed in table 3 represent that sequential administration of the pharmaceutical combination bypasses the intrinsic chemoresistance of tumors cells in vitro. In this invention, the in vitro chemoresistance is considered when the IC50 value reaches values upper than 1000 µM of concentration.

Similar to the in Vitro results, pretreatment with P15 peptide in vivo bypasses the tumor intrinsic chemoresistance (example 4) (FIG. 2A, 2B, 2C).

The P15 peptide ingredient (amino acid sequence: CWMSPRHLGTC SEQ ID NO: 1) has been previously reported as a CK2 inhibitor (Perea S. E., et al. (2004) Antitumor effect of a novel proapoptotic peptide impairing the phosphorylation by the protein kinase CK2. *Cancer Res*. 64:7127-7129). However, this peptide unexpectedly did regulate a group of proteins on tumor cells (Table 4) which reinforce and explain the synergistic antitumor effect of the ingredients among the pharmaceutical combination as well as the chemosensibilization produced by the pretreatment with the P15 peptide. For instance, the P15-regulated proteins play an essential role on the control of tumor cell proliferation and apoptosis and these mechanisms are not the same induced by the rest of the ingredients from this pharmaceutical combination, specifically the cytostatic preferred in this invention.

Likewise, other proteins that are regulated by the ingredient P15 are those involved in the molecular mechanisms of the tumor chemoresistance to the cytostatic preferred in this invention. These unexpected results constitute the molecular basis of the tumor's chemosensibilization produced by this pharmaceutical combination when the ingredients are sequentially administered.

A hallmark in this invention is the fact that effective concentrations of the cytostatic drugs in the pharmaceutical combination are 10- to 100-fold reduced compared to the effective dose when the cytostatic drugs are used alone. It means that a synergistic interaction occurs between the CK2 inhibitor and cytostatic drugs preferred in this invention. Since the practical point of view, this synergistic interaction means that the toxicity of the medicine based on this pharmaceutical combination is much lower than that observed for single cytostatic drugs.

Similarly, the tumor's chemosensibilization elicited after sequential administration of the ingredients from this pharmaceutical combination represents a great advantage as it permits to treat the chemoresistance which is frequently observed in solid tumors and in those ones from hematopoietic origin.

DETAILED EXPOSITION OF THE EXAMPLES

General Procedures

Figure 1:
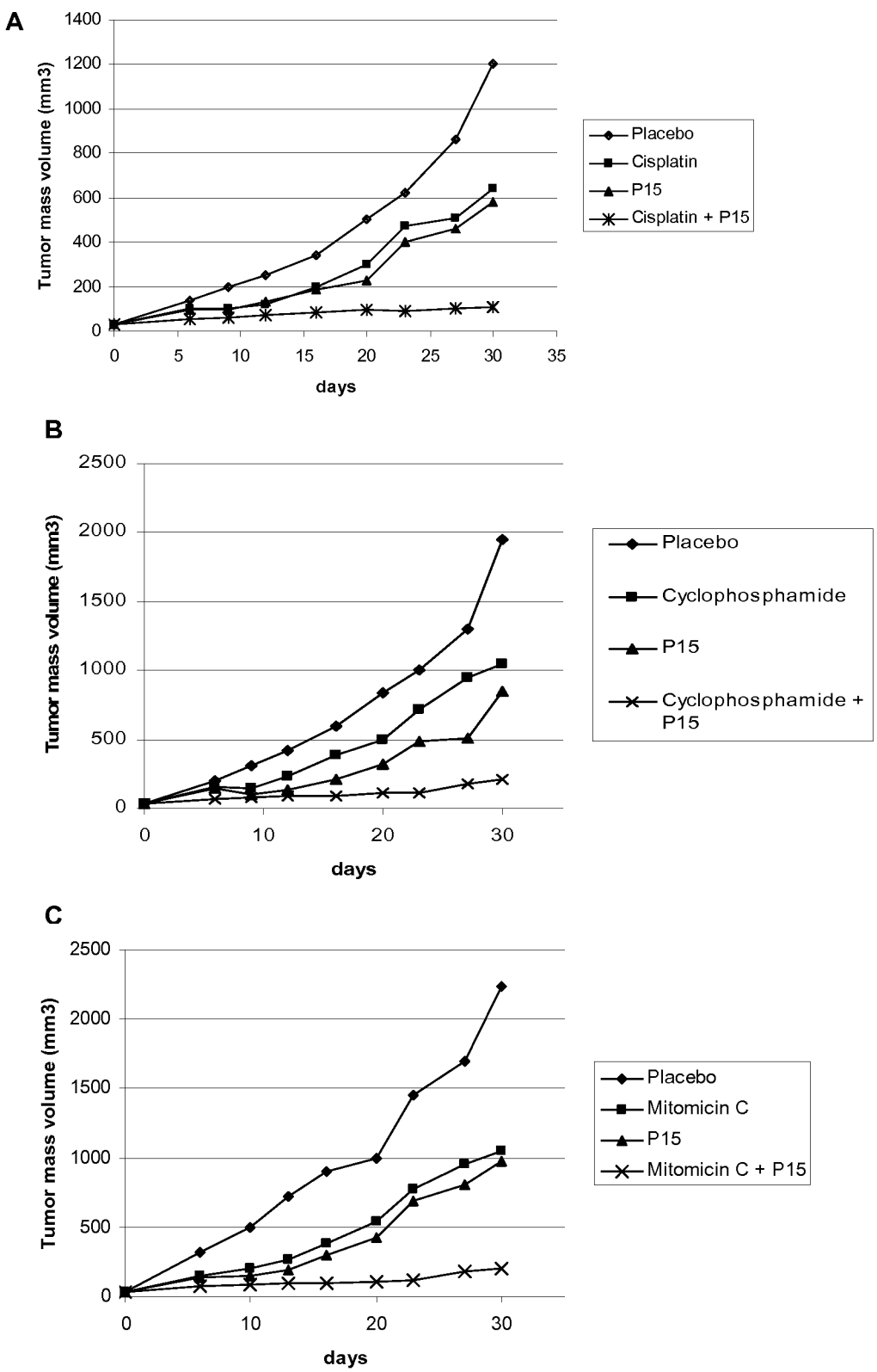
FIG. 1: Potentiation of the antitumor effect by the pharmaceutical combination in a cancer animal model: (A) represents the synergism between cisplatin+P15, (B) represents the synergism between cyclophosphamide+P15, (C) represents the synergism in vivo of mytomicin C+P15.

Cell cultures: The H-125 cell line was arisen from a human Non-Small Cell Lung Carcinoma (NSCLC) and the SW948 cell line was arisen from a human colon carcinoma. Both cell lines were maintained in RPMI 1640 (Gibco) culture medium supplemented with 10% Fetal Calf Serum and y gentamicin (50 μg/ml). Incubation of cell cultures was performed at 37° C. in 5% $CO_2$.

Cell viability assay: For this purpose, 20 μl of Tetrazolium (MTS) (Promega) were added to the cells on each plate. After 2 hours at 37° C., the absorbance at 492 nm was taken. Finally, the IC50 values were estimated from the respective dose-response curves using the "CurveExpert" software.

Cancer animal model: The animal model used in this invention was based on the implantation of human tumors in nude mice (Nu/Nu, BalBC). Briefly, $5 \times 10^6$ H-125 cells were suspended in Phosphate Buffer Solution (PBS) and inoculated subcutaneously. After tumor debut (approx. 30 mm³), treatment was started using the pharmaceutical combination described in this invention. To evaluate the antitumor effect of the pharmaceutical combination, the tumor mass volume was measured and the respective volume was calculated using the formula: $V = widght^2 \times length/2$.

Analysis of the protein profile on the cell extracts: H-125 cells were treated or not with the P15 peptide ingredient of the pharmaceutical combination described in this invention during 40 minutes. Subsequently, cell monolayers were washed with PBS and cells were scrapped from the surface. After two further washes with cold PBS, cellular pellets were resuspended in 10 mM tris-HCl pH 7.5, 0.25M sucrose, 1 mM EGTA+protease inhibitor cocktail and nuclear protein fraction was obtained as previously described (González L. J., et al (2003) Identification of nuclear proteins of small cell lung cancer cell line H82: An improved protocol for the analysis of silver stained proteins. *Electrophoresis* 24:237-252). To analyze the P15-regulated proteins, the respective nuclear protein extracts were alternatively solved by 2D bidimensional gels (pH 4-7) and/or Liquid chromatography (nano HPLC) coupled to Mass spectrometer.

This invention is explained by the following examples:

Example 1

Synergistic Effect of the Combination of P15 Peptide+Conventional Cytostatic Drugs It was evaluated the antineoplastic synergistic effect between the P15 peptide ingredient combined with different cytostatic drugs in the following experimental conditions: H-125 cells were seeded in 96-well plates and P15 peptide was added at 10 and 50 μM to each plate. Simultaneously, each of the cytostatic drugs preferred in this invention was added at doses ranging from 1 to 2000 nM and the incubation was prolonged during 72 hours in the same conditions. Finally, the cell viability and the IC50 values were determined as above described in this invention. Results showed in Table 1 demonstrate that the IC50 values for each cytostatic drug is 10- to 100-fold reduced when simultaneously combined with the ingredient P15 either at 10 or 50 μM. These results clearly demonstrate the potentiation of the antitumor effect of the pharmaceutical combination containing the P15 peptide and the cytostatic drugs preferred in this invention as ingredients.

TABLE 1

Antineoplastic synergistic interaction by the simultaneous administration of the ingredients in this pharmaceutical combination.

| Variant | Cytostatic drug alone | Cytostatic drug + P15 (10 μM) | Cytostatic drug + P15 (50 μM) |
|---|---|---|---|
| Cisplatin | 720 nM | 530 nM | 40 nM |
| Paclitaxel | 17 nM | 8 nM | 3 nM |
| 5-Fluouracil | 1200 nM | 420 nM | 60 nM |
| Vincristin | 856 nM | 100 nM | 8 nM |
| Doxorubicin | 423 nM | 200 nM | 76 nM |
| Cyclophosphamide | 2400 nM | 1004 nM | 85 nM |
| Mitomicin C | 994 nM | 93 nM | 9 nM |
| Imatinib | 600 nM | 200 nM | 58 nM |
| Velcade | 2000 nM | 1200 nM | 700 nM |
| Iressa | 689 nM | 174 nM | 47 nM |

Example 2

Potentiation of the Antitumor Effect by the Pharmaceutical Combination in a Cancer Animal Model For this purpose, $5 \times 10^6$ H-125 tumor cells were implanted as above mentioned in this invention in 6-8 week-old BalBc nude mice. After tumor debut, the ingredients of the pharmaceutical combination were administered as follow: The P15 peptide in saline solution was administered intraperitoneal at 0.5 mg/kg/day during 5 days. Concomitantly, intraperitoneal injection of cisplatin (FIG. 1A), or cyclophosphamide (FIG. 1B) or Mytomicin (FIG. 1C) were performed at 1 mg/kg/day in the same frequency. The cytostatic drugs are also solved in saline solution. Tumor volume was registered as described above in this invention. The results showed in FIGS. 1A, 1B and 1C indicate that the pharmaceutical combination potentiate the antitumor effect when ingredients are simultaneously administered and as it was observed by the complete tumor regression. Otherwise, when ingredients are administered as monotherapy only a marginal antitumor effect was observed respect to the Placebo group. Thus, we further demonstrate the synergistic interaction between the ingredients among this pharmaceutical combination in an outstanding preclinical cancer model.

Example 3

Effect of P15 Peptide in Bypassing the In Vitro Chemoresistance

In this assay we evaluated the effect of the pharmaceutical combination in bypassing the chemoresistance phenomenon when ingredients are sequentially administered. For this purpose, H-125 cells were seeded at 2000 cells/well in 96-well plates and after 24 hours 20 μM of the P15 peptide was added. After 16 hours of incubation with the P15 peptide ingredient, cell monolayers were washed twice with saline solution. Finally, the cytostatic drugs preferred in this invention were added at concentration ranging from 1 to 2000 nM and the incubation was prolonged during 72 hours. At the end, cell viability and the IC50 values for each cytostatic drug were determined as previously described in this invention. Results displayed in Table 2 demonstrate that pre-treatment of tumor cells with the P15 peptide ingredient increases the sensitivity of these cells to each of the cytostatic drugs preferred in this invention. Furthermore, we evaluated the effect of P15 pre-treatment on SW948 cells which are intrinsically resistant to the effect of the cytostatic drugs. Results demonstrated that the P15 peptide ingredient also converts to the intrinsic drug-refractory tumor cells into sensitive cells to the cytostatic drugs preferred in this invention. (Table 3).

Our data demonstrate that the sequential administration of the P15 peptide ingredient respect to the cytostatic drugs preferred in this invention leads to the sensibilization of tumor cells to the antineoplastic effect of such drugs.

TABLE 2

In vitro chemosensibilization of the pharmaceutical combination by sequential administration of the ingredients

| Variants | Cytostatic drug alone | Cytostatic drug + P15 pre-treatment |
|---|---|---|
| Cisplatin | 720 nM | 20 nM |
| Paclitaxel | 17 nM | 0.9 nM |
| 5-Fluouracil | 1200 nM | 105 nM |
| Vincristin | 856 nM | 83 nM |
| Doxorubicin | 423 nM | 72 nM |
| Cyclophosphamide | 2400 nM | 100 nM |
| Mitomicin C | 994 nM | 20 nM |
| Imatinib | 600 nM | 10 nM |
| Velcade | 2000 nM | 370 nM |
| Iressa | 689 nM | 63 nM |

TABLE 3

In vitro chemosensibilization of the pharmaceutical combination by sequential administration of the ingredients on intrinsic drug-refractory tumor cells

| Variants | Cytostatic drug alone | Cytostatic drug + P15 pre-treatment |
|---|---|---|
| Cisplatin | ≥1000 μM | 120 μM |
| Paclitaxel | ≥1000 μM | 97 μM |
| Doxorubicin | ≥1000 μM | 320 μM |

The effect of the P15 peptide ingredient on the chemosensibilization is further verified by the drug-regulated protein profile observed on the tumor cells used in this invention. For this purpose, nuclear protein extracts coming from H-125 cells treated or not with the P15 peptide ingredient were analyzed as previously described in this invention. Table 4 displays a group of proteins which are regulated by the P15 peptide ingredient and because of their known function; it reinforces the molecular basis for the tumor's chemosensibilization produced by this peptide in the pharmaceutical combination in this invention.

TABLE 4

P15-regulated protein profile

| Down-regulated proteins by the P15 peptide ingredient | Inhibition rate |
|---|---|
| Nucleofosmin | 48 |
| T-Plastin | 3.34 |
| Heat Shock Proteins (HSP-27, -70 y -90) | 2.5 |
| Y-box1 transcription factor | 3.33 |
| Eritropoietin precursor | 120 |
| S-gluthathione transferase | 4.87 |
| Proteasome activator complex | 3.35 |
| Ubiquitin activated E1 enzyme | 2.49 |
| Glucose-6-phosphate isomerase | 8.53 |
| Gliceraldehyde 6-phosphate deshydrogenase | 6.62 |
| Piruvate kinase | 8.34 |
| Translational controled tumor protein | 4.32 |

| Up-regulated proteins by the P15 peptide ingredient | Activation rate |
|---|---|
| Prohibitin | 2.28 |
| Tubulin alpha-1 | 3.23 |
| Tubulin beta-2 | 2.56 |
| Tubulin beta-3 | 3.15 |

Example 4

In Vivo Chemosensibilization Produced by the P15 Peptide Ingredient

Figure 2:
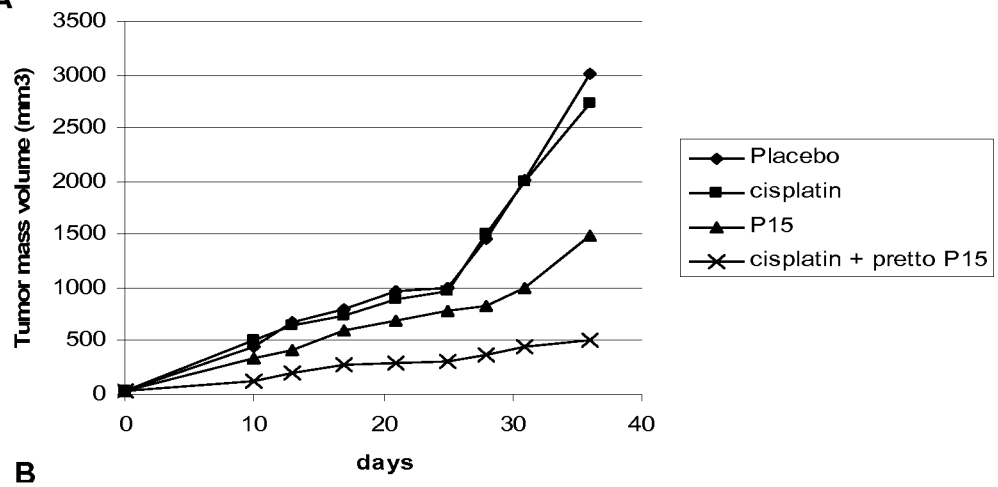
FIG. 2: Effect of tumor's chemosensibilization by the P15 peptide in vivo: (A) represents the bypassing of chemoresistance toward cisplatin, (B) represents the bypassing of chemoresistance toward paclitaxel and (C) represents the bypassing of chemoresistance toward doxorubicin.
Figure 2:
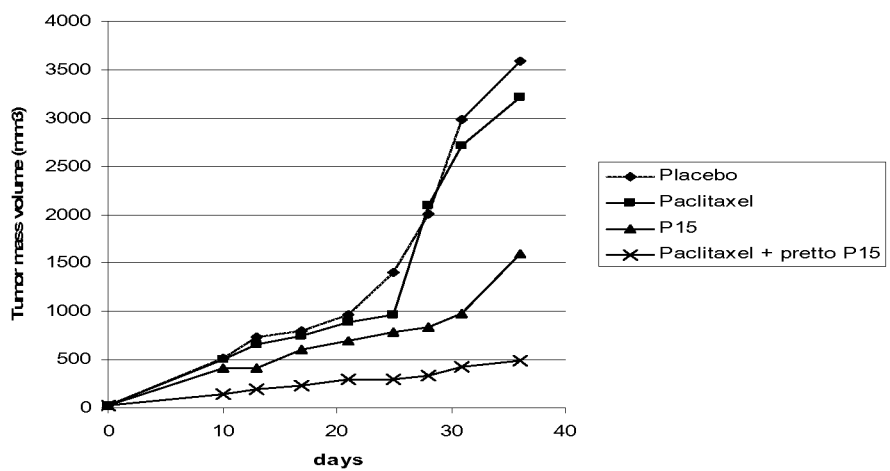
Figure 2:
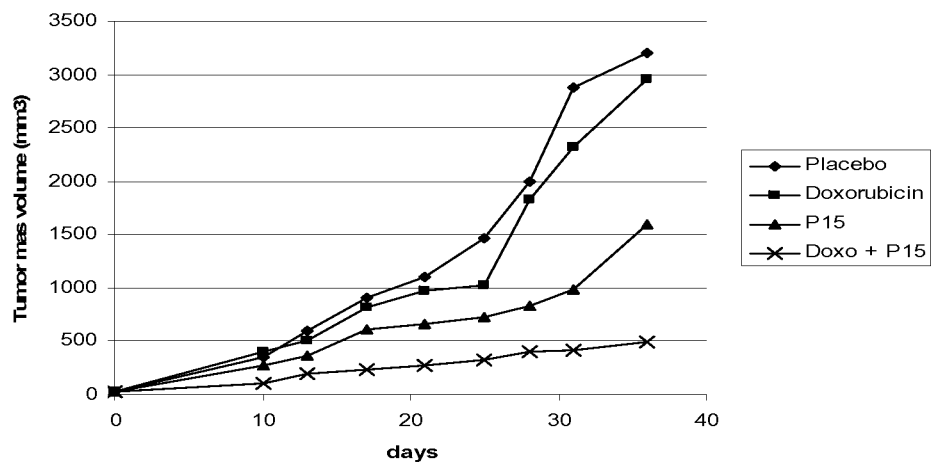

For this purpose, $5 \times 10^6$ SW948 cells were implanted in nude mice as previously described in this invention. After tumor debut the pharmaceutical combination was sequentially administered as follow: First, the P15 peptide ingredient was administered intraperitoneal at 0.5 mg/kg/day during 5 days. Subsequently, cisplatin (FIG. 2A), Paclitaxel (FIG. 2B) and doxorubicin (FIG. 2C) were administered at 5 mg/kg/day during further 5 days. The results here demonstrate that the in vivo P15 pre-treatment is able to revert the chemorefractory phenotype of the tumors which become responsible to the cytostatic drugs preferred in this invention. These findings also provide the evidences that the pharmaceutical combination in this invention is able to bypass the commonly observed intrinsic tumor resistance when the ingredients are sequentially administered.

INCORPORATION OF SEQUENCE LISTING

Incorporated herein by reference in its entirety is the Sequence Listing for the application. The Sequence Listing is disclosed on a computer-readable ASCII text file titled, "sequence_listing.txt", created on Apr. 10, 2014. The sequence_listing.txt file is 1 kb in size.

The invention claimed is:

1. A pharmaceutical combination kit for simultaneous, staggered or sequential administration, said kit comprising the P15 peptide identified as SEQ ID NO: 1, and a cytostatic drug selected from the group consisting of: Cisplatin, Paclitaxel, 5-Fluorouracil, Vincristin, Vinblastin, Doxorubicin, Docetaxel, Cyclophosphamide, Mitomycin C, Imatinib, Bortezomib and Iressa.

2. The pharmaceutical combination kit according to the claim 1, wherein the cytostatic drug is 5-Fluorouracil.

3. The pharmaceutical combination kit according to the claim 1, wherein the cytostatic drug is doxorubicin.

4. The pharmaceutical combination kit according to the claim 1, wherein the cytostatic drug is cyclophosphamide.

5. The pharmaceutical combination kit according to the claim 1, wherein the cytostatic drug is Mitomycin C.

6. The pharmaceutical combination kit according to the claim 1, wherein the cytostatic drug is bortezomib.

7. The pharmaceutical combination kit according to the claim 1, wherein the cytostatic drug is Iressa.

8. The pharmaceutical kit combination according to the claim 1, wherein the cytostatic drug is Imatinib.

9. The pharmaceutical combination kit according to claim 1, wherein cytostatic drug is cisplatin.

10. The pharmaceutical combination kit according to claim 1, wherein cytostatic drug is paclitaxel or docetaxel.

11. The pharmaceutical combination kit according to claim 1, wherein cytostatic drug is vincristin or vinblastin.

* * * * *

UNITED STATES PATENT AND TRADEMARK OFFICE
CERTIFICATE OF CORRECTION

PATENT NO. : 8,871,725 B2  
APPLICATION NO. : 12/280629  
DATED : October 28, 2014  
INVENTOR(S) : Perea Rodriguez et al.

It is certified that error appears in the above-identified patent and that said Letters Patent is hereby corrected as shown below:

Title page, item 73, assignee

Now reads: "Centro de Ingeniería Genética y Biotecnología, Ciudad de La Habana (CU)"

Should read: -- Centro de Ingeniería Genética y Biotecnología, Ciudad de La Habana (CU) and BIOREC S.A., Montevideo (UY) --

Signed and Sealed this  
Thirteenth Day of October, 2015

Michelle K. Lee  
*Director of the United States Patent and Trademark Office*